(12) United States Patent
He et al.

(10) Patent No.: US 12,153,038 B2
(45) Date of Patent: Nov. 26, 2024

(54) TEST SYSTEM AND TEST METHOD FOR REPLACING NATURAL GAS HYDRATE WITH CARBON DIOXIDE

(71) Applicant: Institute of Geology and Geophysics, Chinese Academy of Sciences, Beijing (CN)

(72) Inventors: Jianming He, Beijing (CN); Shouding Li, Beijing (CN); Xiao Li, Beijing (CN); Zhaobin Zhang, Beijing (CN)

(73) Assignee: Institute of Geology and Geophysics, Chinese Academy of Sciences, Beijing (CN)

(*) Notice: Subject to any disclaimer, the term of this patent is extended or adjusted under 35 U.S.C. 154(b) by 249 days.

(21) Appl. No.: 17/981,514

(22) Filed: Nov. 7, 2022

(65) Prior Publication Data

US 2023/0408482 A1  Dec. 21, 2023

(30) Foreign Application Priority Data

Jun. 16, 2022 (CN) .......................... 202210686210.5

(51) Int. Cl.
| | |
|---|---|
| *G01N 33/24* | (2006.01) |
| *G01N 30/02* | (2006.01) |
| *G01N 30/06* | (2006.01) |
| *G01N 30/24* | (2006.01) |

(52) U.S. Cl.
CPC ............ *G01N 33/241* (2013.01); *G01N 30/06* (2013.01); *G01N 30/24* (2013.01); *G01N 2030/025* (2013.01)

(58) Field of Classification Search
CPC .. G01N 2030/025; G01N 30/06; G01N 30/24; G01N 33/241; Y02P 90/70; E21B 49/00; E21B 41/0099; E21B 43/164; E21B 2200/20
See application file for complete search history.

(56) References Cited

FOREIGN PATENT DOCUMENTS

| | | | | |
|---|---|---|---|---|
| CN | 110306952 A | * | 10/2019 | ......... E21B 41/0099 |
| CN | 114542021 A | * | 5/2022 | |

* cited by examiner

*Primary Examiner* — John Fitzgerald
*Assistant Examiner* — Truong D Phan
(74) *Attorney, Agent, or Firm* — Bochner PLLC; Andrew Bochner; Eric Kleinertz

(57) ABSTRACT

A test system and a test method for replacing natural gas hydrate with carbon dioxide are disclosed, relating to the technical field of exploitation of natural gas hydrates. The test system comprises a sample reaction vessel, a sample boundary condition loading device, a methane gas supply device, a carbon dioxide gas supply device, an output article collection and measurement device, and a data acquisition control device. A sample-sealing rubber sleeve and an upper sample-sealing plate are arranged in an inner cavity of the vessel, the sample-sealing rubber sleeve, a lower tray and the upper sample-sealing plate form a sample-sealing space. An axial pressure loading plate is arranged on the upper sample-sealing plate, and an upper cover plate is provided with an axial pressure loading injection hole. A side shrouding is provided with a confining pressure loading injection hole and a product discharge hole.

18 Claims, 3 Drawing Sheets

TEST SYSTEM AND TEST METHOD FOR REPLACING NATURAL GAS HYDRATE WITH CARBON DIOXIDE

CROSS REFERENCE TO RELATED APPLICATION

This patent application claims the benefit and priority of Chinese Patent Application No. 202210686210.5 filed on Jun. 16, 2022, the disclosure of which is incorporated by reference herein in its entirety as part of the present application.

TECHNICAL FIELD

The present disclosure relates to the technical field of exploitation of natural gas hydrates, and in particular to a test system and test method for replacing natural gas hydrates with carbon dioxide.

BACKGROUND ART

Natural gas hydrates are distributed in deep-sea shallow sediments and terrestrial permafrost zones, with huge resources and dominated by methane hydrates. The phase development curves of the methane hydrate and the carbon dioxide hydrate can form an intersection point. As hydrate decomposition is a heat absorption process, carbon dioxide hydrate is more stable in the temperature and pressure range below the intersection point, while methane hydrate will be decomposed into methane gas and water, and the ambient temperature and pressure of natural hydrates are also in this range, it is feasible to develop hydrate reservoirs by using a method for replacing methane with carbon dioxide under a specific temperature and pressure environment, and more stable carbon dioxide hydrates can be produced after the completion of the replacement reaction. There is no quantitative evaluation about the efficiency and process of the replacement of natural gas hydrates with the carbon dioxide, the influencing factors of the replacement of natural gas hydrates with the carbon dioxide are not clear enough, lacking relevant experimental simulation equipment. Therefore, it is necessary to form a system for simulating exploitation of natural gas hydrates by carbon dioxide replacement in a laboratory.

SUMMARY

An objective of the present disclosure is to provide a test system and test method for replacing natural gas hydrate with carbon dioxide to solve the problems in the prior art. In accordance with the system and method provided by the present disclosure, the carbon dioxide sustainable replacement test for natural gas hydrates can be carried out in a laboratory to provide guidance for the exploitation of natural gas hydrates by carbon dioxide replacement.

To achieve the objective above, the present disclosure provides the following technical solutions:

A test system for replacing natural gas hydrate with carbon dioxide provided by the present disclosure comprises a sample reaction vessel, a sample boundary condition loading device, a methane gas supply device, a carbon dioxide gas supply device, an output article collection and measurement device, and a data acquisition control device.

The sample reaction vessel comprises a side shrouding, and an upper cover plate arranged at a top of the side shrouding and a lower tray arranged at a bottom of the side shrouding. The side shrouding, the upper cover and the lower tray form an inner cavity of the vessel. A sample-sealing rubber sleeve and a upper sample-sealing plate are arranged in the inner cavity of the vessel, a lower end of the sample-sealing rubber sleeve is hermetically connected to the lower tray, an upper end of the sample-sealing rubber sleeve is hermetically connected to the upper sample-sealing plate, and the sample-sealing rubber sleeve, the upper sample-sealing plate and the lower tray form a sample-sealing space. An axial pressure loading plate capable of moving up and down is arranged in the inner cavity of the vessel above the upper sample-sealing plate, and the upper cover plate is provided with an axial pressure loading injection hole. The side shrouding is provided with a confining pressure loading injection hole and a product discharge hole and is sleeved with a liquid cooling jacket. The product discharge hole penetrates through the sample-sealing rubber sleeve to communicate with the sample-sealing space. A methane gas injection pipe penetrates through the upper cover plate, the axial pressure loading plate and the upper sample-sealing plate to extend into the sample-sealing space. A carbon dioxide injection pipe penetrates through the lower tray to extend into the sample-sealing space. The lower tray is provided with a temperature and pressure sensor for detecting the temperature and pressure in the sample-sealing space.

The sample boundary condition loading device comprises an axial pressure loading device and a confining pressure loading device. The axial pressure loading device and the confining pressure loading device are respectively connected to the axial pressure loading injection hole and the confining pressure loading injection hole via pipelines. The pipeline between the axial pressure loading device and the axial pressure loading injection hole is provided with an axial pressure transmitter, and the pipeline between the confining pressure loading device and the confining pressure loading injection hole is provided with a confining pressure transmitter.

The methane gas supply device comprises a methane gas cylinder. A pipeline, connected to the methane gas injection pipe, of the methane gas cylinder is provided with a first gas booster pump, a first constant-pressure or constant-rate gas pump and a first gas storage tank in sequence, and the first gas booster pump is close to the methane gas cylinder. The first gas storage tank is placed in a first cold bath device, and the first cold bath device is connected to a first temperature control device. The pipeline between the first gas storage tank and the methane gas injection pipe is provided with a first gas pressure transmitter.

The carbon dioxide gas supply device comprises a carbon dioxide gas cylinder. A pipeline, connected to the carbon dioxide injection pipe, of the carbon dioxide gas cylinder is provided with a second gas booster pump, a second constant-pressure or constant-rate gas pump and a second gas storage tank in sequence, and the second gas booster pump is close to the carbon dioxide gas cylinder. The second gas storage tank is placed in a second cold bath device, and the second cold bath device is connected to a second temperature control device. The pipeline between the second gas storage tank and the carbon dioxide injection pipe is provided with a second gas pressure transmitter.

The output article collection and measurement device comprises a pressure control valve, preset pressurizing equipment, and an output article collection and measurement assembly. The product discharge hole is connected to the pressure control valve via a pipeline. The pressure control valve is connected to the output article collection and measurement assembly via a pipeline. The output article collection and measurement assembly is configured for collecting and measuring the output article. The pressure control valve is also connected to the preset pressurizing equipment via a pressure switch.

The temperature and pressure sensor, the axial pressure loading device, the confining pressure loading device, the axial pressure transmitter, the confining pressure transmitter, the first constant-pressure or constant-rate gas pump, the second constant-pressure or constant-rate gas pump, the first temperature control device, the second temperature control device, the first gas pressure transmitter, the second gas pressure transmitter and the output article collection and measurement assembly are electrically connected to the data acquisition control device.

Preferably, a sliding rod is connected to a top end of the axial pressure loading plate, the sliding rod penetrates through the upper cover plate to extend outwards, and a through hole penetrating through the sliding rod and the axial pressure loading plate is provided in the sliding rod. The methane gas injection pipe is installed in the through hole, and a lower end of the methane gas injection pipe penetrates through the upper sample-sealing plate to extend to the bottom of the sample-sealing space. A portion, extending into the sample-sealing space, of the methane gas injection pipe is provided with a plurality of gas holes in a height direction of the sample-sealing space. A pipeline holder is installed at a top end of the upper cover plate, and an upper end of the methane gas injection pipe is held and fixed to the pipeline holder.

Preferably, a top end, extending into the sample-sealing space, of the carbon dioxide injection pipe is provided with a plurality of gas holes. The carbon dioxide injection pipe comprises a carbon dioxide injection pipe for an upper portion of sample, a carbon dioxide injection pipe for a middle portion of sample and a carbon dioxide injection pipe for a lower portion of sample, top ends of which extend to the upper portion, the middle portion and the lower portion of the sample-sealing space respectively. A gas outlet pipeline of the second gas storage tank is divided into three branches which are respectively connected to the carbon dioxide injection pipe for an upper portion of sample, the carbon dioxide injection pipe for a middle portion of sample and the carbon dioxide injection pipe for a lower portion of sample. Each branch is provided with a gas injection control valve.

Preferably, the temperature and pressure sensor comprises a temperature and pressure sensor for an upper portion of sample, a temperature and pressure sensor for a middle portion of sample and a temperature and pressure sensor for a lower portion of sample, and measuring probes of the temperature and pressure sensor for an upper portion of sample, the temperature and pressure sensor for a middle portion of sample and the temperature and pressure sensor for a lower portion of sample are respectively located at the upper portion, the middle portion and the lower portion of the sample-sealing space.

Preferably, the output article collection and measurement device further comprises a desander. The desander is arranged on a pipeline between the product discharge hole and the pressure control valve, and a pipeline between the desander and the product discharge hole is provided with an output gas switch valve. The output article collection and measurement assembly comprises a water-gas separator, a gas chromatograph, a gas collection valve, a cold trap treatment device, a gas-liquid separation valve, and a gas collection pump. An inlet of the water-gas separator is connected to an outlet of the pressure control valve, an electronic balance is arranged at a bottom of a water outlet of the water-gas separator, a gas outlet of the water-gas separator is divided into two paths, one path is connected to an inlet of the gas chromatograph via an automatic control valve, and the other path is connected to an inlet of the gas collection valve. An outlet of the gas chromatograph is connected to the inlet of the gas collection valve. The gas chromatograph, the cold trap treatment device and the gas collection pump are all electrically connected to the data acquisition control device.

Preferably, the pipeline between the first gas storage tank and the methane gas injection pipe is further provided with a first automatic pressure and gas volume sensor and a methane gas switch valve, and a vacuum pump is further connected to the pipeline between the first gas storage tank and the methane gas injection pipe via a vacuumizing switch valve. The pipeline between the second gas storage tank and the carbon dioxide injection pipe is further provided with a second automatic pressure and gas volume sensor and a carbon dioxide switch valve. A pipeline between the outlet of the gas chromatograph and the inlet of the gas collection valve is further provided with a third automatic pressure and gas volume sensor. A fourth automatic pressure and gas volume sensor is connected to the tail end of the gas collection pump. The first automatic pressure and gas volume sensor, the second automatic pressure and gas volume sensor, the third automatic pressure and gas volume sensor and the fourth automatic pressure and gas volume sensor are all electrically connected to the data acquisition control device.

Preferably, the axial pressure loading device comprises a first large-displacement continuous liquid supply plunger pump set and a first pressure servo continuous liquid supply plunger pump set, inlets of the first large-displacement continuous liquid supply plunger pump set and the first pressure servo continuous liquid supply plunger pump set are connected to an oil source, and outlets of the first large-displacement continuous liquid supply plunger pump set and the first pressure servo continuous liquid supply plunger pump set are divided into two paths comprising an axial pressure loading pipeline and an axial pressure unloading pipeline. The axial pressure loading pipeline is connected to the axial pressure loading injection hole and is provided with an axial pressure loading control valve, and the axial pressure unloading pipeline is connected to the oil source and is provided with an axial pressure unloading control valve. The confining pressure loading device comprises a second large-displacement continuous liquid supply plunger pump set and a second pressure servo continuous liquid supply plunger pump set, inlets of the second large-displacement continuous liquid supply plunger pump set and the second pressure servo continuous liquid supply plunger pump set are connected to the oil source, and outlets of the second large-displacement continuous liquid supply plunger pump set and the second pressure servo continuous liquid supply plunger pump set are divided into two paths comprising a confining pressure loading pipeline and a confining pressure unloading pipeline. The confining pressure loading pipeline is connected to the confining pressure loading injection hole and is provided with a confining pressure loading control valve, and the confining pressure unloading pipeline is connected to the oil source and is provided with a confining pressure unloading control valve.

Preferably, an outlet pipeline of the methane gas cylinder is provided with a first pressure regulating valve, and an inlet pipeline and an outlet pipeline of the first gas booster pump are respectively provided with a first gas switch valve and a second gas switch valve. An outlet pipeline of the carbon dioxide gas cylinder is provided with a second pressure regulating valve, and an inlet pipeline and an outlet pipeline of the second gas booster pump are respectively provided with a third gas switch valve and a fourth gas switch valve.

Preferably, the data acquisition control device comprises a multi-path data receiver, a digital closed-loop servo controller and a computer control terminal. The multi-path data receiver and the digital closed-loop servo controller are both electrically connected to the computer control terminal. The first automatic pressure and gas volume sensor, the second automatic pressure and gas volume sensor, the third automatic pressure and gas volume sensor, the fourth automatic pressure and gas volume sensor, the cold trap processing device and the gas collection pump are all electrically connected to the multi-path data receiver. The gas chromatograph is electrically connected to the computer control terminal. The temperature and pressure sensor, the axial pressure loading device, the confining pressure loading device, the axial pressure transmitter, the confining pressure transmitter, the first constant-pressure or constant-rate air pump, the second constant-pressure or constant-rate air pump, the first temperature control device, the second temperature control device, the first air pressure transmitter, and the second gas pressure transmitter are all electrically connected to the digital closed-loop servo controller.

A test method for replacing natural gas hydrate with carbon dioxide based on the test system for replacing natural gas hydrate with carbon dioxide above is further provided, comprising the following steps:

S1: filling the sample-sealing rubber sleeve with sandy soil sample mixed with deionized water, and installing the sample reaction vessel;

S2: activating the axial pressure loading device and the confining pressure loading device to apply axial pressure and confining pressure on the sandy soil sample simultaneously enabling the axial pressure and confining pressure to reach set target pressure values; activating liquid circulation in the liquid cooling jacket to make the temperature in the sample-sealing space to meet a test temperature environment requirement;

S3: vacuumizing the methane gas inlet pipeline, opening the methane gas cylinder, and activating the first gas booster pump, the first constant-pressure or constant-rate gas pump and the first temperature control device, making the methane gas entering the first gas storage tank to reach a set target pressure value and a set target temperature value; injecting the methane gas from the first gas storage tank into the sandy soil sample via the methane gas injection pipe, enabling a reaction to generate a methane hydrate sample, and stopping injecting the methane gas after the reaction is finished; and S4: completely removing air in the carbon dioxide gas inlet pipeline, opening the carbon dioxide gas cylinder, activating the second gas booster pump, the second constant-pressure or constant-rate gas pump and the second temperature control device, making the carbon dioxide gas entering the second gas storage tank to reach a set target pressure value and a set target temperature value; adjusting the preset pressurizing equipment to a pressure value for the carbon dioxide replacement reaction and activating the pressure switch, injecting the carbon dioxide gas from the second gas storage tank into the methane hydrate sample via the carbon dioxide injection pipe for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device via the product discharge hole, and the output article is collected and measured by the output article collection and measurement assembly.

Compared with the prior art, the present disclosure has the following technical effects:

According to the test system and test method for replacing natural gas hydrate with carbon dioxide, for the demands of a natural gas hydrate sample for the controlled temperature and pressure boundary condition loading, a sample-sealing rubber sleeve with a certain thickness is used to form a sample-sealing space with a certain deformation capacity in conjunction with a upper sample-sealing plate. The axial pressure and the confining pressure of the sample are independently controlled by a data acquisition control device and a pressure transmitter to achieve pressure environment simulation, and a fluid circulates in a liquid cooling jacket outside a sample reaction vessel for realizing temperature environment simulation. For the control requirements of methane hydrate sample synthesis and subsequent carbon dioxide replacement reaction on the temperature and pressure of the methane and carbon dioxide gas, a constant-pressure or constant-rate gas pump, a pressure transmitter and the data acquisition control device are adopted to control the gas pressure; a cold bath device, a temperature control device and the data acquisition control device are adopted to control the gas temperature, and a pressure control valve and preset pressurizing equipment are arranged at the end of an output article collection pipeline to control the discharge pressure of mixed gas. Therefore, the pressure in a sealed space of a methane hydrate sample is accurately controlled to guarantee the sustainability of the carbon dioxide replacement test.

Furthermore, for the slow preparation of methane hydrate sample due to a hydrate synthesis rate, a methane gas injection pipeline is provided with a plurality of gas holes in a sample height direction to accelerate the synthesis process of the methane hydrate. For the slow process of carbon dioxide replacement reaction and the surface effect which may retard the subsequent reaction, carbon dioxide gas injection multi-pipelines are used to inject carbon dioxide gas into the sample in layers to achieve the sustainability of the replacement reaction process. For the changes of gas volume and pressure during the whole test process, a plurality of automatic pressure and gas volume sensors are arranged in a gas inlet pipeline and a gas production pipeline of the sealed sample to monitor the changes of gas flow and pressure during the whole test process, and form a monitoring network with a multi-path data receiver to monitor and record the gas flow and pressure data during the whole test process. For the component changes of the gas mixture produced after the replacement reaction and the safety management, an automatic control valve and a gas chromatograph are used to monitor the component changes of the gas mixture at a fixed frequency, and a cold trap treatment device is used to recover most of the gas mixture produced from the test in conjunction with a gas collection pump.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings in the following description show merely some embodiments of the present disclosure, and a person of ordinary skill in the art may still derive other drawings from these accompanying drawings without creative efforts.

Figure 1:
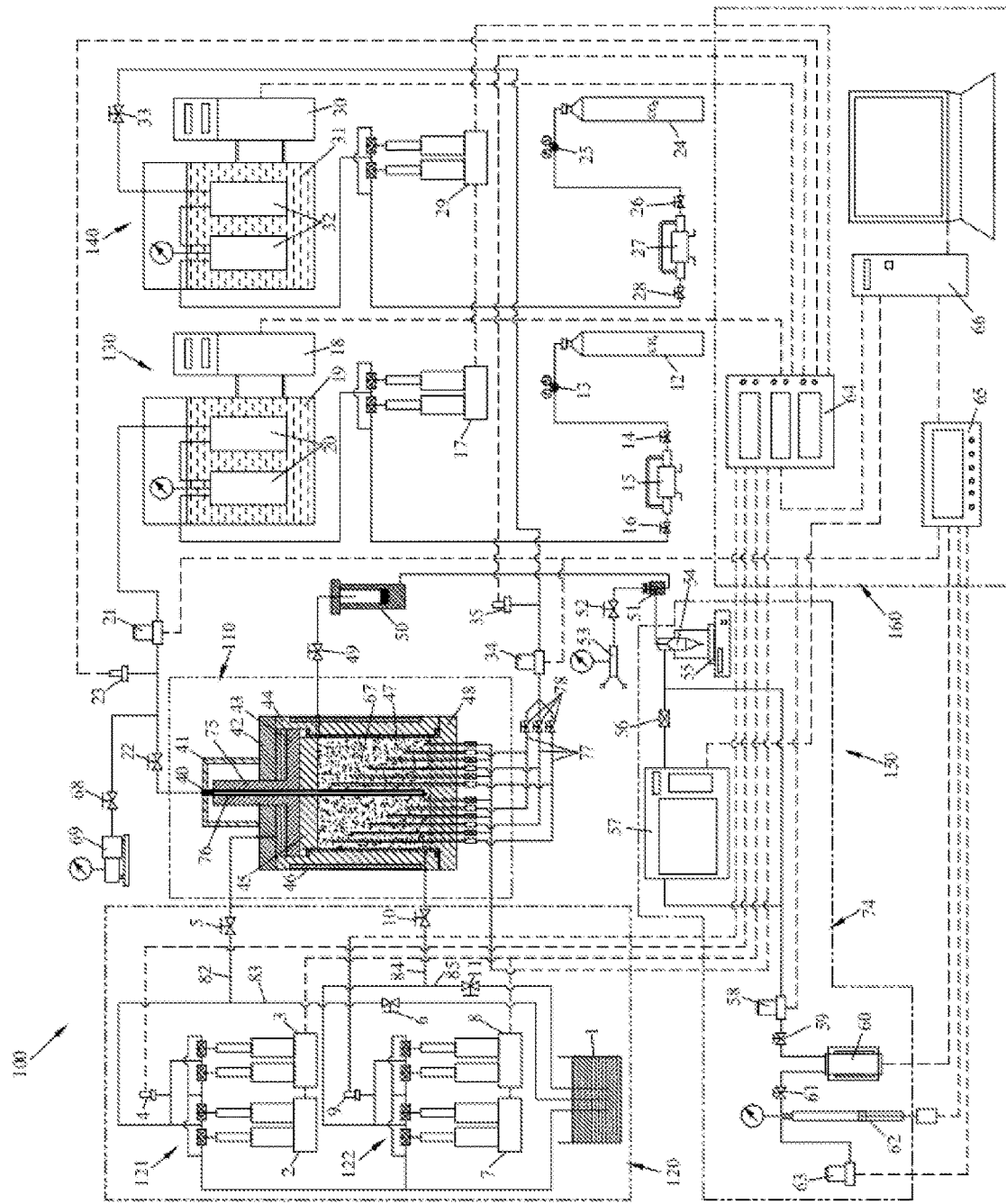
FIG. 1 is a structure diagram of a test system for replacing natural gas hydrate with carbon dioxide in accordance with the present disclosure.

In the drawings: 100—test system for replacing natural gas hydrate with carbon dioxide; 110—sample reaction vessel; 120—sample boundary condition loading device; 121—axial pressure loading device; 122—confining pressure loading device; 130—methane gas supply device; 140—carbon dioxide gas supply device; 150—output article collection and measurement device; 160—data acquisition and control device; 1—oil source; 2—first large-displacement continuous liquid supply plunger pump set; 3—first pressure servo continuous liquid supply plunger pump set; 4—axial pressure transmitter; 5—axial pressure loading control valve; 6—axial pressure unloading control valve; 7—second large-displacement continuous liquid supply plunger pump set; 8—second pressure servo continuous liquid supply plunger pump set; 9—confining pressure transmitter; pressure loading control valve; 11—confining pressure unloading control valve; 12—methane gas cylinder; 13—first pressure regulating valve; 14—first gas switch valve; 15—first gas booster pump; 16—second gas switch valve; 17—first constant-pressure or constant-rate gas pump; 18—first temperature control device; 19—first cold bath device; gas storage tank; 21—first automatic pressure and gas volume sensor; 22—methane gas switch valve; 23—first gas pressure transmitter; 24—carbon dioxide gas cylinder; 25—second pressure regulating valve; 25—third gas switch valve; 27—second gas booster pump; 28—fourth gas switch valve; 29—second constant-pressure or constant-rate gas pump; 30—second temperature control device; 31—second cold bath device; 32—second gas storage tank; 33—carbon dioxide switch valve; 34—second automatic pressure and gas volume sensor; 35—second gas pressure transmitter; 36—carbon dioxide injection pipe for an upper portion of sample; 37—carbon dioxide injection pipe for a middle portion of sample; 38—carbon dioxide injection pipe for a lower portion of sample; 39—temperature and pressure sensor; 40—methane gas injection pipe; 41—pipeline holder; 42—upper cover plate; 43—axial pressure loading plate; 44—side shrouding; sample-sealing plate; 46—liquid cooling jacket; 47—sample-sealing rubber sleeve; 48—lower tray; 49—an output gas switch valve; 50—de-sander; 51—pressure control valve; 52—pressure switch; 53—preset pressurizing equipment; 54—water-gas separator; balance; 56—automatic control valve; 57—gas chromatograph; 58—third automatic pressure and gas volume sensor; 59—gas collection valve; 60—cold trap processing device; 61—gas-liquid separation valve; 62—gas collection pump; 63—fourth automatic pressure and gas volume sensor; 64—digital closed loop servo controller; data receiver; 66—computer control terminal; 67—methane hydrate sample; 68—vacuumizing switch valve; 69—vacuum pump; 70—axial pressure loading injection hole; 71—confining pressure loading injection hole; 72—product discharge hole; 73—carbon dioxide injection hole; 74—output collecting and measuring assembly; rod; 76—through hole; 77—branch; 78—gas injection control valve; 79—temperature and pressure sensor for an upper portion of sample; 80—temperature and pressure sensor for a middle portion of sample; 81—temperature and pressure sensor for a lower portion of sample; 82—axial pressure loading pipeline; 83—axial pressure unloading pipeline; 84—confining pressure loading pipeline; 85—confining pressure unloading pipeline.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

An objective of the present disclosure is to provide a test system and test method for replacing natural gas hydrate with carbon dioxide to solve the problems in the prior art. In accordance with the system and method provided by the present disclosure, the carbon dioxide sustainable replacement test for natural gas hydrates can be carried out in a laboratory to provide guidance for the exploitation of natural gas hydrates by carbon dioxide replacement.

To make the objectives, features and advantages of the present disclosure more apparent and understandable, the following further describes the present disclosure in detail with reference to the accompanying drawings and specific embodiments.

Figure 2:
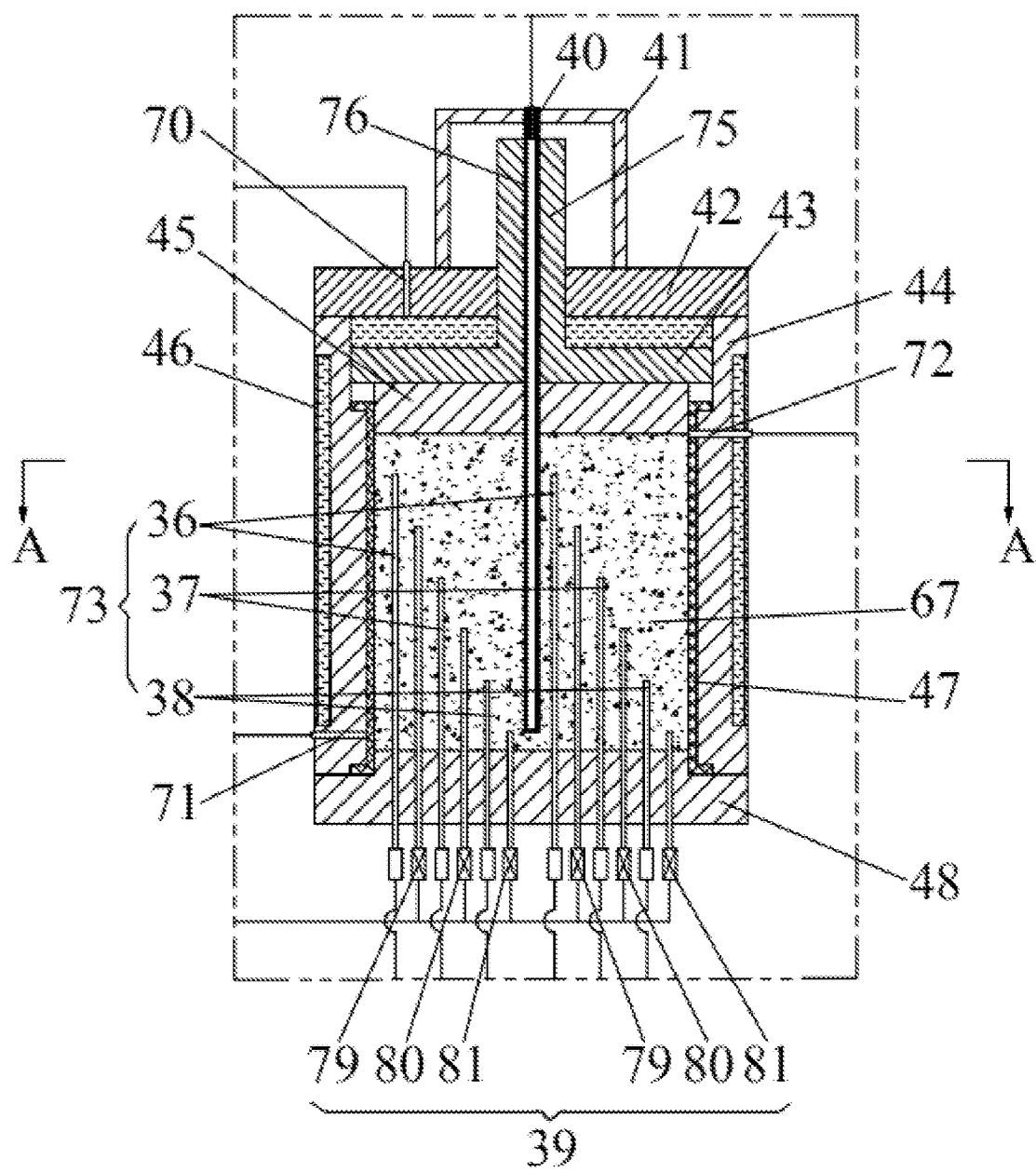
FIG. 2 is a structure diagram of a sample reaction vessel in accordance with the present disclosure.
Figure 3:
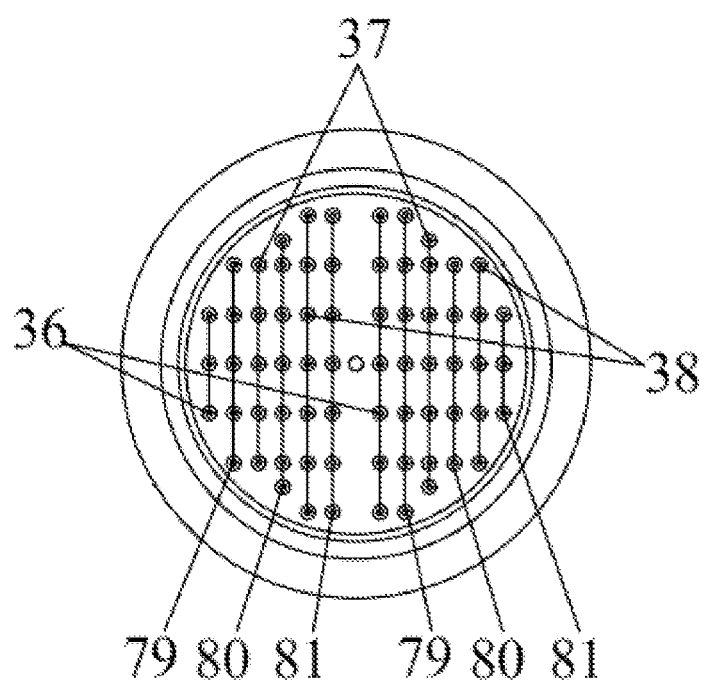
FIG. 3 is a sectional diagram of A-A of the sample reaction vessel in FIG. 2.

As shown in FIG. 1 to FIG. 3, this embodiment provides a test system 100 for replacing natural gas hydrate with carbon dioxide, comprising a sample reaction vessel 110, a sample boundary condition loading device 120, a methane gas supply device 130, a carbon dioxide gas supply device 140, an output article collection and measurement device 150, and a data acquisition control device 160;

The sample reaction vessel 110 comprises a side shrouding 44, and an upper cover plate 42 arranged at the top of the side shrouding 44 and a lower tray 48 arranged at the bottom of the side shrouding 44. The side shrouding 44, the upper cover 42 and the lower tray 48 form an inner cavity of the vessel. A sample-sealing rubber sleeve 47 and a upper sample-sealing plate 45 are arranged in the inner cavity of the vessel, the lower end of the sample-sealing rubber sleeve 47 is hermetically connected to the lower tray 48, the upper end of the sample-sealing rubber sleeve 47 is hermetically connected to the upper sample-sealing plate 45, and the sample-sealing rubber sleeve 47, the upper sample-sealing plate 45 and the lower tray 48 form a sample-sealing space. An axial pressure loading plate 43 capable of moving up and down is arranged in the inner cavity of the vessel above the upper sample-sealing plate 45, and the upper cover plate 42 is provided with an axial pressure loading injection hole 70. The side shrouding 44 is provided with a confining pressure loading injection hole 71 and a product discharge hole 72 and is sleeved with a liquid cooling jacket 46. The product discharge hole 72 penetrates through the sample-sealing rubber sleeve 47 to communicate with the sample-sealing space. A methane gas injection pipe 40 penetrates through the upper cover plate 42, the axial pressure loading plate 43 and the upper sample-sealing plate 45 to extend into the sample-sealing space. A carbon dioxide injection pipe 73 penetrates through the lower tray 48 to extend into the sample-sealing space. The lower tray 48 is provided with a temperature and pressure sensor 39 for detecting the temperature and pressure in the sample-sealing space;

The sample boundary condition loading device 120 comprises an axial pressure loading device 121 and a confining pressure loading device 122. The axial pressure loading device 121 and the confining pressure loading device 122 are respectively connected to the axial pressure loading injection hole 70 and the confining pressure loading injection hole 71 via pipelines. The pipeline between the axial pressure loading device 121 and the axial pressure loading injection hole 70 is provided with an axial pressure transmitter 4, and the pipeline between the confining pressure loading device 122 and the confining pressure loading injection hole 71 is provided with a confining pressure transmitter 9;

The methane gas supply device 130 comprises a methane gas cylinder 12. A pipeline, connected to the methane gas injection pipe 40, of the methane gas cylinder 12 is provided with a first gas booster pump 15, a first constant-pressure or constant-rate gas pump 17 and a first gas storage tank 20 in sequence, and the first gas booster pump is close to the methane gas cylinder 12. The first gas storage tank 20 is placed in a first cold bath device 19, and the first cold bath device 19 is connected to a first temperature control device 18. The pipeline between the first gas storage tank 20 and the methane gas injection pipe 40 is provided with a first gas pressure transmitter 23;

The carbon dioxide gas supply device 140 comprises a carbon dioxide gas cylinder 24. A pipeline, connected to the carbon dioxide injection pipe 73, of the carbon dioxide gas cylinder 24 is provided with a second gas booster pump 27, a second constant-pressure or constant-rate gas pump 29 and a second gas storage tank 32 in sequence, and the second gas booster pump 27 is close to the carbon dioxide gas cylinder 24. The second gas storage tank 32 is placed in a second cold bath device 31, and the second cold bath device 31 is connected to a second temperature control device 30. The pipeline between the second gas storage tank 32 and the carbon dioxide injection pipe 73 is provided with a second gas pressure transmitter 35;

The output article collection and measurement device 150 comprises a pressure control valve 151, preset pressurizing equipment 53, and an output article collection and measurement assembly 74. The product discharge hole 72 is connected to the pressure control valve 51 via a pipeline. The pressure control valve 51 is connected to the output article collection and measurement assembly 74 via a pipeline. The output article collection and measurement assembly 74 is used for collecting and measuring the output. The pressure control valve 51 is also connected to the preset pressurizing equipment 53 via a pressure switch 52;

The temperature and pressure sensor 39, the axial pressure loading device 121, the confining pressure loading device 122, the axial pressure transmitter 4, the confining pressure transmitter 9, the first constant-pressure or constant-rate gas pump 17, the second constant-pressure or constant-rate gas pump 29, the first temperature control device 18, the second temperature control device 30, the first gas pressure transmitter 23, the second gas pressure transmitter 35 and the output article collection and measurement assembly 74 are electrically connected to the data acquisition control device 160.

In this embodiment, a sliding rod 75 is connected to the top end of the axial pressure loading plate 43, the sliding rod 75 penetrates through the upper cover plate 42 to extend outwards, and a through hole 76 penetrating through the sliding rod 75 and the axial pressure loading plate 43 is provided in the sliding rod 75. The methane gas injection pipe 40 is installed in the through hole 76, and the lower end of the methane gas injection pipe 40 penetrates through the upper sample-sealing plate 45 to extend to the bottom of the sample-sealing space. A portion, extending into the sample-sealing space, of the methane gas injection pipe 40 is provided with a plurality of gas holes in a height direction of the sample-sealing space. A pipeline holder 41 is installed at the top end of the upper cover plate 42, and the upper end of the methane gas injection pipe 40 is held and fixed to the pipeline holder 41.

In this embodiment, the top end, extending into the sample-sealing space, of the carbon dioxide injection pipe 73 is provided with a plurality of gas holes. The carbon dioxide injection pipe 73 comprises a carbon dioxide injection pipe for an upper portion of sample 36, a carbon dioxide injection pipe for a middle portion of sample 37 and a carbon dioxide injection pipe for a lower portion of sample 38, the top ends of which extend to the upper portion, the middle portion and the lower portion of the sample-sealing space respectively. A gas outlet pipeline of the second gas storage tank 32 is divided into three branches 77 which are respectively connected to the carbon dioxide injection pipe for an upper portion of sample 36, the carbon dioxide injection pipe for a middle portion of sample 37 and the carbon dioxide injection pipe for a lower portion of sample 38. Each branch 77 is provided with a gas injection control valve 78.

In this embodiment, the temperature and pressure sensor 39 comprises a temperature and pressure sensor for an upper portion of sample 79, a temperature and pressure sensor for a middle portion of sample 80 and a temperature and pressure sensor for a lower portion of sample 81, and measuring probes of the temperature and pressure sensor for an upper portion of sample 79, the temperature and pressure sensor for a middle portion of sample 80 and the temperature and pressure sensor for a lower portion of sample 81 are respectively located at the upper portion, the middle portion and the lower portion of the sample-sealing space.

In this embodiment, the output article collection and measurement device 150 further comprises a desander 50. The desander 50 is arranged on a pipeline between the product discharge hole 72 and the pressure control valve 51, and a pipeline between the desander 50 and the product discharge hole 72 is provided with an output gas switch valve 49. The output article collection and measurement assembly 74 comprises a water-gas separator 54, a gas chromatograph 57, a gas collection valve 59, a cold trap treatment device 60, a gas-liquid separation valve 61, and a gas collection pump 62. An inlet of the water-gas separator 54 is connected to an outlet of the pressure control valve 51, an electronic balance 55 is arranged at the bottom of a water outlet of the water-gas separator 54, a gas outlet of the water-gas separator 54 is divided into two paths, one path is connected to an inlet of the gas chromatograph 57 via an automatic control valve 56, and the other path is connected to an inlet of the gas collection valve 59. An outlet of the gas chromatograph 57 is connected to the inlet of the gas collection valve 59. The gas chromatograph 57, the cold trap treatment device 60 and the gas collection pump 62 are all electrically connected to the data acquisition control device 160.

In this embodiment, the pipeline between the first gas storage tank 20 and the methane gas injection pipe 40 is further provided with a first automatic pressure and gas volume sensor 21 and a methane gas switch valve 22, and a vacuum pump 69 is further connected to the pipeline between the first gas storage tank 20 and the methane gas injection pipe 40 via a vacuumizing switch valve 68. The pipeline between the second gas storage tank 32 and the carbon dioxide injection pipe 73 is further provided with a second automatic pressure and gas volume sensor 34 and a carbon dioxide switch valve 33. A pipeline between the outlet of the gas chromatograph 57 and the inlet of the gas collection valve 59 is further provided with a third automatic pressure and gas volume sensor 58. A fourth automatic pressure and gas volume sensor 63 is connected to the tail end of the gas collection pump 62. The first automatic pressure and gas volume sensor 21, the second automatic pressure and gas volume sensor 34, the third automatic pressure and gas volume sensor 58 and the fourth automatic pressure and gas volume sensor 63 are all electrically connected to the data acquisition control device 160.

In this embodiment, the axial pressure loading device 121 comprises a first large-displacement continuous liquid supply plunger pump set 2 and a first pressure servo continuous liquid supply plunger pump set 3, inlets of the first large-displacement continuous liquid supply plunger pump set 2 and the first pressure servo continuous liquid supply plunger pump set 3 are connected to an oil source 1, and outlets of the first large-displacement continuous liquid supply plunger pump set and the first pressure servo continuous liquid supply plunger pump set are divided into two paths, namely an axial pressure loading pipeline 82 and an axial pressure unloading pipeline 83. The axial pressure loading pipeline 82 is connected to the axial pressure loading injection hole 70 and is provided with an axial pressure loading control valve 5, and the axial pressure unloading pipeline 83 is connected to the oil source 1 and is provided with an axial pressure unloading control valve 6. The confining pressure loading device 122 comprises a second large-displacement continuous liquid supply plunger pump set 7 and a second pressure servo continuous liquid supply plunger pump set 8, inlets of the second large-displacement continuous liquid supply plunger pump set 7 and the second pressure servo continuous liquid supply plunger pump set 8 are connected to the oil source 1, and outlets of the second large-displacement continuous liquid supply plunger pump set and the second pressure servo continuous liquid supply plunger pump set are divided into two paths, namely a confining pressure loading pipeline 84 and a confining pressure unloading pipeline 85. The confining pressure loading pipeline 84 is connected to the confining pressure loading injection hole 71 and is provided with a confining pressure loading control valve 10, and the confining pressure unloading pipeline 85 is connected to the oil source 1 and is provided with a confining pressure unloading control valve 11.

In this embodiment, an outlet pipeline of the methane gas cylinder 12 is provided with a first pressure regulating valve 13, and an inlet pipeline and an outlet pipeline of the first gas booster pump 15 are respectively provided with a first gas switch valve 14 and a second gas switch valve 16. An outlet pipeline of the carbon dioxide gas cylinder 24 is provided with a second pressure regulating valve 25, and an inlet pipeline and an outlet pipeline of the second gas booster pump 27 are respectively provided with a third gas switch valve 26 and a fourth gas switch valve 28.

In this embodiment, the data acquisition control device 160 comprises a multi-path data receiver 65, a digital closed-loop servo controller 64 and a computer control terminal 66. The multi-path data receiver 65 and the digital closed-loop servo controller 64 are both electrically connected to the computer control terminal 66. The first automatic pressure and gas volume sensor 21, the second automatic pressure and gas volume sensor 34, the third automatic pressure and gas volume sensor 58, the fourth automatic pressure and gas volume sensor 63, the cold trap processing device 60 and the gas collection pump 62 are all electrically connected to the multi-path data receiver 65. The gas chromatograph 57 is electrically connected to the computer control terminal 66. The temperature and pressure sensor 39, the axial pressure loading device 121, the confining pressure loading device 122, the axial pressure transmitter 4, the confining pressure transmitter 9, the first constant-pressure or constant-rate air pump 17, the second constant-pressure or constant-rate air pump 29, the first temperature control device 18, the second temperature control device 30, the first air pressure transmitter 23 and the second gas pressure transmitter 35 are all electrically connected to the digital closed-loop servo controller 64.

In this embodiment, the capacity of the oil source 1 must meet the oil quantity demands of large-displacement continuous liquid supply plunger pump sets (the first large-displacement continuous liquid supply plunger pump set 2 and the second large-displacement continuous liquid supply plunger pump set 7) and pressure servo continuous liquid supply plunger pump sets (the first pressure servo continuous liquid supply plunger pump set 3 and the second pressure servo continuous liquid supply plunger pump set 8), thus completing the axial pressure and confining pressure loading requirements of the hydrate sample 67. The first large-displacement continuous liquid supply plunger pump set 2 and the first pressure servo continuous liquid supply plunger pump set 3 cooperate with each other to meet the requirements for time and precision of the hydrate sample 67 in the axial pressure loading process. The second large-displacement continuous liquid supply plunger pump set 7 and the second pressure servo continuous liquid supply plunger pump set 8 cooperate with each other to meet the requirements for time and precision of the hydrate sample 67 in the confining pressure loading process. The axial pressure loading plate 43 and the upper sample-sealing plate 45 should be in close contact to ensure that an axial load acts on the hydrate sample 67. The upper sample-sealing plate 45, the sample-sealing rubber sleeve 47 and the lower tray 48 form a sealed space for the hydrate sample 67. The frequency response of the digital closed-loop servo controller 64 should be in consistent with the frequency response of the axial pressure transmitter 4 and the confining pressure transmitter 9, and should meet the requirements for the axial pressure and confining pressure servo loading of the hydrate sample 67. The sample-sealing rubber sleeve 47 should have a certain of thickness and flexibility and can be tightly combined with the upper sample-sealing plate 45 and the lower tray 48 to form the closed space, allowing the sample to have a certain deformation under the action of the axial pressure and confining pressure. A fluid circulates in the liquid cooling jacket 46 outside the vessel so as to guarantee requirements of the sealed vessel for the temperature environment in the test process.

In this embodiment, liquid methane in the methane gas cylinder 12 is regulated by the first pressure regulating valve 13 and then enters the first gas booster pump 15 in a gaseous state to be pressurized. The computer control terminal 66 sends an instruction to the digital closed-loop servo controller 64 to control the first constant-pressure or constant-rate gas pump 17 to supply gas at a constant pressure or a constant flow rate. The computer control terminals 66 sends an instruction to the digital closed-loop servo controller 64 to control the first temperature control device 18 to adjust the temperature for a cold bath of the first cold bath device 19. The forming process of the methane hydrate sample 67 can be monitored by the temperature and pressure sensors 39 arranged at multiple locations in the sample-sealing space. The evolution process of the hydrate synthesis boundary is determined by inversely calculating a temperature field and a pressure field by monitoring the temperature and pressure data in the sample space. The methane gas injection pipe 40 is provided with gas holes along a height of the sample, and thus the methane gas in the pipeline can evenly seep into the sample along the full height of the sample.

In this embodiment, liquid carbon dioxide in the carbon dioxide gas cylinder 24 is regulated by the second pressure regulating valve 25 and then enters the second gas booster pump 27 in a gaseous state to be pressurized, and the pressurized gas is regulated by the second constant-pressure or constant-rate gas pump 29 and then is input into the second gas storage tank 32 at a constant pressure or a constant flow rate. The computer control terminals 66 sends an instruction to the digital closed-loop servo controller 64 to control the second constant-pressure or constant-rate air pump 29 to supply gas at a constant pressure or a constant flow speed, and the computer control terminals 66 sends an instruction to the digital closed-loop servo controller 64 to control the second temperature control device 30 to adjust the temperature for a cold bath of the second cold bath device 31. In this way, carbon dioxide gas with the temperature and pressure set by the computer control terminal 66 is stored in the second gas storage tank 32 and used for replacing methane molecules in the methane hydrate to produce methane gas, the set temperature and pressure values ensure both the occurring of the carbon dioxide replacement reaction and the stability of the methane hydrate specimen 67 without decomposition. The carbon dioxide injection pipe for an upper portion of sampleline 36, the carbon dioxide injection pipe for a middle portion of sampleline 37 and the carbon dioxide injection pipe for a lower portion of sampleline 38 should be opened in sequence, with the interval between opening depending on the carbon dioxide replacement reaction. The temperature and pressure sensors 39 (the sample upper part temperature and pressure sensor 79, the sample middle part temperature and pressure sensor 80 and the sample lower part temperature and pressure sensor 81) arranged at multiple locations in the sample-sealing space are used to monitor the replacement reaction in the sample-sealing space and determining the evolution process of the replacement reaction. The sequential carbon dioxide injection can effectively avoid the surface effect of carbon dioxide replacement reaction, the surface effect can retard the further generation of the replacement reaction. After the replacement reaction, methane molecules with smaller density are transported to the top of the sample and are then discharged by an output gas switch valve 49, while the carbon dioxide with larger density can be retained inside the specimen to continue the replacement reaction. The pipeline deep into the methane hydrate specimen 67 is provided with gas holes at its tail end for a certain length, and thus the carbon dioxide gas in the pipeline can evenly seep into the sample through the tail end of the pipeline for replacement reaction.

In this embodiment, the temperature and pressure sensors 39 are arranged at different locations in the sample space, and the temperature and pressure data are collected by the multi-path data receiver 65 and then input to the computer control terminal 66, such that the changes of the temperature field and pressure field in the sample space can be speculated and calculated by obtaining temperature and pressure values of the multi-point locations in the hydrate sample space.

In this embodiment, the desander 50 is used for removing sandy soil in a sample attached to a gas output, the capacity of which can meet the sand output amount in the test process. The pressure control valve 51 is used for keeping a pressure value set by the preset pressurizing equipment 53 at a gas product output end, such that the pressure in the test system, during the carbon dioxide replacement test of the natural gas hydrate, is kept within a range in which the replacement test can occur. The water-gas separator 54 is used for separating water from the produced water-gas mixture, and the mass of the water is measured by the electronic balance 55. The automatic control valve 56 measures the component changes of the produced mixed gas at a fixed sampling frequency in conjunction with the gas chromatograph 57, the final produced gas enters the cold trap treatment device 60 via the gas collection valve 59 for supercooling condensation capture, and the condensed residual gas enters the gas collection pump 62 via the gas-liquid separation valve 61 to be recovered again. Finally, the extremely small amount of gas which cannot be recovered is directly discharged into air after being monitored and recorded by the fourth automatic pressure and gas amount sensor 63, and the gas volume recovered by the cold trap treatment device 60 and the gas collection pump 62 is recorded and received by the multi-path data receiver 65, and then stored in the computer control terminal 66.

The automatic pressure and gas volume sensor only measures and provides data, so is connected to the multi-path data receiver 65 and is only responsible for the measurement and providing of data. While the task of the pressure transmitter is to judge whether the pressure in the pipeline reaches a preset pressure value, and to provide a signal to the digital closed-loop servo controller 64, the digital closed-loop servo controller 64 is used to control whether the pump sets continue to apply pressure, if the pressure is insufficient, then the pump sets continue to pressurize; or if the pressure reaches the standard, then the pump sets stop pressurizing.

A test method for replacing natural gas hydrate with carbon dioxide based on the test system for replacing natural gas hydrate with carbon dioxide above is further provided, comprising the following steps:

S1: filling the sample-sealing rubber sleeve 47 with sandy soil sample mixed with deionized water, and installing the sample reaction vessel 110;

S2: activating the axial pressure loading device 121 and the confining pressure loading device 122 to apply axial pressure and confining pressure on the sandy soil sample simultaneously, making the axial pressure and confining pressure to reach set target pressure values; activating liquid circulation in the liquid cooling jacket 46 to make the temperature in the sample-sealing space to meet a test temperature environment requirement;

S3: vacuumizing the methane gas inlet pipeline, opening the methane gas cylinder 12, and activating the first gas booster pump 15, the first constant-pressure or constant-rate gas pump 17 and the first temperature control device 18, making the methane gas entering the first gas storage tank 20 to reach a set target pressure value and a set target temperature value; injecting the methane gas from the first gas storage tank 20 into the sandy soil sample via the methane gas injection pipe 40, enabling a reaction to generate a methane hydrate sample 67, and stopping injecting the methane gas after the reaction is finished; and S4: completely removing air in the carbon dioxide gas inlet pipeline, opening the carbon dioxide gas cylinder 24, activating the second gas booster pump 27, the second constant-pressure or constant-rate gas pump 29 and the second temperature control device 30, making the carbon dioxide gas entering the second gas storage tank 32 to reach a set target pressure value and a set target temperature value; adjusting the preset pressurizing equipment 53 to a pressure value for the carbon dioxide replacement reaction and turning on the pressure switch 52, injecting the carbon dioxide gas from the second gas storage tank 32 into the methane hydrate sample 67 via the carbon dioxide injection pipe 73 for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device 150 via the product discharge hole 72, and the output article is collected and measured by the output article collection and measurement assembly 74.

The following further explains and describes the test process of the present disclosure in conjunction with specific embodiments:

1, A sandy soil material with specified grading conditions is employed to simulate ocean sediments, deionized water is added into the sandy soil material according to water consumption calculated for preparing a methane hydrate sample 67, a sample-sealing rubber sleeve 47 is placed into a space formed by a side shrouding 44 and a lower tray 48, and the sandy soil material mixed with the deionized water is placed into the sample-sealing rubber sleeve 47 layer by layer; then a methane gas injection pipe 40 is inserted into the top of the sample, a upper sample-sealing plate 45 is tightly combined with a sample-sealing rubber sleeve 47 to seal a sample, and an axial pressure loading plate 43, an upper cover plate 42 and a pipeline holder 41 are continuously installed in sequence; and finally, the methane gas injection pipe at the upper part of the vessel, sample axial pressure and confining pressure loading pipelines and a test gas output pipeline are connected, and after the pipeline connection is completed, all liquid path and gas path valves in the test system are confirmed to be in a closed state.

2. An axial pressure loading control valve 5 and a confining pressure loading control valve 10 are opened, target pressure values of the axial pressure and the confining pressure of the sample are set by a computer control terminal 66, thus enabling a digital closed-loop servo controller 64 to turn on a first large-displacement continuous liquid supply plunger pump set 2 and a second large-displacement continuous liquid supply plunger pump set 7 to load the axial pressure and the confining pressure for the sample at the same time. Pressure values of axial pressure and confining pressure for a sample are measured by an axial pressure transmitter 4 and a confining pressure transmitter 9 during the loading, and then transmitted to the digital closed-loop servo controller 64 via a signal cable to be compared with the target pressure values. When the axial pressure and the confining pressure are close to the target pressure values, the digital closed-loop servo controller 64 sends an instruction via a signal cable to turn off the first large-displacement continuous liquid supply plunger pump set 2 and the second large-displacement continuous liquid supply plunger pump set 7 and turn on a first pressure servo continuous liquid supply plunger pump set 3 and a second pressure servo continuous liquid supply plunger pump set 8; the axial pressure and the confining pressure can accurately reach the set target pressure values in a slow loading mode, and the pressurizing control process is repeated in the subsequent test process to achieve the purpose of servo of the stress boundary of the sample. The liquid circulation in the liquid cooling jacket 46 outside the vessel is initiated to meet the requirements for the temperature environment in the sealed vessel during the test.

3. A second gas switch valve 16, a methane gas switch valve 22 and a vacuumizing switch valve 68 are opened, a vacuum pump 69 is turned on, and the vacuumizing switch valve 68 and the methane gas switch valve 22 are closed after the air in the methane gas inlet pipeline is completely removed, and then a first pressure regulating valve 13 is regulated and a first gas switch valve 14 is opened, thus enabling methane gas from a methane gas cylinder 12 to enter a first gas booster pump 15. A target pressure value and a target temperature value of a first gas storage tank 20 are set by the computer control terminal 66, a second gas switch valve 16 is opened, a first constant-pressure or constant-rate pump 17 and a first temperature control device 18 are turned on by the digital closed-loop servo controller 64, thus enabling the methane gas entering the first gas storage tank 20 to reach the set target pressure value and the set target temperature value. The methane gas switch valve 22 is opened to make the methane gas from the first gas storage tank 20 evenly seep into the sandy soil sample via the methane gas injection pipe 40. The first gas pressure transmitter 23 measures a methane gas pressure value and transmits the methane gas pressure value to the digital closed-loop servo controller 64 via a signal cable to be compared with a target pressure value, and the first constant-pressure or constant-rate gas pump 17 is turned on at any time to reach a set pressure value, thus guaranteeing that the methane gas and a sandy soil sample can react to generate a methane hydrate sample 67. A first automatic pressure and gas quantity sensor 21 monitors and records the flow rate and pressure of methane gas entering a sample space, the flow rate and pressure data of the methane gas are received by the multi-path data receiver 65 and stored in the computer control terminal 66, and the temperature and pressure data are also received by the multi-path data receiver 65 and stored in the computer control terminal 66. The methane gas switch valve 22 can be closed upon completion of the methane hydrate formation process as determined by temperature and pressure changes, thus the methane hydrate sample 67 is prepared and is available for subsequent carbon dioxide replacement reaction.

4. A second pressure regulating valve 25 is regulated to discharge the carbon dioxide gas from a carbon dioxide gas cylinder 24, a third gas switch valve 26, a fourth gas switch valve 28, a carbon dioxide switch valve 33, a gas collection valve 59 and a gas separation valve 61 are opened to enable the carbon dioxide gas to flow along the entire gas pipeline until it is discharged from the fourth automatic pressure and gas volume sensor 63 to the atmosphere for a period of time. After the air in the pipeline is completely discharged, the fourth gas switch valve 28, the carbon dioxide switch valve 33, the gas collection valve 59 and the gas separation valve 61 are closed, and the second gas booster pump 27 is turned on. A target pressure value and a target temperature value of a second gas storage tank 32 are set by the computer control terminal 66, the fourth gas switch valve 28 is opened to enable the digital closed-loop servo controller 64 to activate a second constant pressure or constant speed gas pump 29 and a second temperature control device 30, making the carbon dioxide gas entering the second storage tank 32 reach the set target pressure value and the set temperature value. Preset pressurizing equipment 53 is regulated to a pressure value for the carbon dioxide replacement reaction, and a pressure switch 52, the carbon dioxide switch valve 33 and a gas injection control valve 78 corresponding to a carbon dioxide injection pipe for an upper portion of sample 36 are opened, an output gas switch valve 49, the gas collection valve 59 and the gas-liquid separation valve 61 are opened, such that the carbon dioxide gas enters the upper space of the hydrate sample 67 from the second storage tank 32 for replacement reaction. A second automatic pressure and gas volume sensor 34 monitors and records the flow rate and pressure of the carbon dioxide gas entering the sample space, the flow rate and pressure data of the carbon dioxide gas are received by the multi-path data receiver 65 and stored in the computer control terminal 66. The second gas pressure transmitter 35 measures the pressure value of the carbon dioxide gas and transmits the pressure of the carbon dioxide to the digital close-loop servo controller 64 via a signal cable to be compared with the target pressure value. A second constant-pressure or constant-rate gas pump 29 is turned on at any time to reach a set pressure value, thus guaranteeing the normal operation of the carbon dioxide replacement reaction. After the replacement reaction in the sample upper space is basically completed, the gas injection control valve 78 corresponding to a carbon dioxide injection pipe for an upper portion of sampleline 36 is closed, and the gas injection control valve 78 corresponding to a carbon dioxide injection pipe for a middle portion of sampleline 37 is opened to make the replacement reaction continue. After the replacement reaction in the sample middle space is basically completed, the gas injection control valve 78 corresponding to the carbon dioxide injection pipe for a middle portion of sampleline 37 is closed, and the gas injection control valve 78 corresponding to a carbon dioxide injection pipe for a lower portion of sampleline 38 is opened. After the replacement reaction in the sample lower space is basically completed, the gas injection control valve 78 corresponding to the carbon dioxide injection pipe for a lower portion of sampleline 38 is closed, the gas mixture of the methane and carbon dioxide gas produced by the replacement reaction enters a desander 50 via an output gas switch valve 49, and then enters a water-gas separator 54 via a pressure control valve 51. The water yield is measured by an electronic balance 55. An automatic control valve 56 is opened at a certain frequency to measure gas content changes of methane and carbon dioxide in the gas mixture by the gas chromatograph 57. The second automatic pressure and gas volume sensor 34 monitors and records the flow rate and pressure of the produced gas mixture, the flow rate and pressure data of the gas mixture are received by the multi-path data receiver 65 and stored in the computer control terminal 66, and then the gas mixture enters a cold trap treatment device 60 via the gas collection valve 59 for condensation and recovery, and then the residual gas enters a gas collection pump 62 via the gas-liquid separation valve 61 for further recovery, and finally an extremely small amount of gas is discharged directly into the air via a fourth automatic pressure and gas volume sensor 63.

Several examples are used for illustration of the principles and implementation methods of the present disclosure. The description of the embodiments is merely used to help illustrate the method and its core principles of the present disclosure. In addition, a person of ordinary skill in the art can make various modifications in terms of specific embodiments and scope of application in accordance with the teachings of the present disclosure. In conclusion, the content of this specification shall not be construed as a limitation to the present disclosure.

What is claimed is:

1. A test system for replacing natural gas hydrate with carbon dioxide, comprising a sample reaction vessel, a sample boundary condition loading device, a methane gas supply device, a carbon dioxide gas supply device, an output article collection and measurement device, and a data acquisition control device;
   the sample reaction vessel comprises a side shrouding, an upper cover plate arranged at a top of the side shrouding and a lower tray arranged at a bottom of the side shrouding; the side shrouding, the upper cover and the lower tray form an inner cavity of the vessel; a sample-sealing rubber sleeve and a upper sample-sealing plate are arranged in the inner cavity of the vessel, a lower end of the sample-sealing rubber sleeve is hermetically connected to the lower tray, an upper end of the sample-sealing rubber sleeve is hermetically connected to the upper sample-sealing plate, and the sample-sealing rubber sleeve, the upper sample-sealing plate and the lower tray form a sample-sealing space; an axial pressure loading plate capable of moving up and down is arranged in the inner cavity of the vessel above the upper sample-sealing plate, and the upper cover plate is provided with an axial pressure loading injection hole; the side shrouding is provided with a confining pressure loading injection hole and a product discharge hole and is sleeved with a liquid cooling jacket; the product discharge hole penetrates through the sample-sealing rubber sleeve to communicate with the sample-sealing space; a methane gas injection pipe penetrates through the upper cover plate, the axial pressure loading plate and the upper sample-sealing plate to extend into the sample-sealing space; a carbon dioxide injection pipe penetrates through the lower tray to extend into the sample-sealing space; the lower tray is provided with a temperature and pressure sensor for detecting the temperature and pressure in the sample-sealing space;
   the sample boundary condition loading device comprises an axial pressure loading device and a confining pressure loading device; the axial pressure loading device and the confining pressure loading device are respectively connected to the axial pressure loading injection hole and the confining pressure loading injection hole via pipelines, the pipeline between the axial pressure loading device and the axial pressure loading injection hole is provided with an axial pressure transmitter, and the pipeline between the confining pressure loading device and the confining pressure loading injection hole is provided with a confining pressure transmitter;
   the methane gas supply device comprises a methane gas cylinder; a pipeline, connected to the methane gas injection pipe, of the methane gas cylinder is provided with a first gas booster pump, a first constant-pressure or constant-rate gas pump and a first gas storage tank in sequence, and the first gas booster pump is close to the methane gas cylinder; the first gas storage tank is placed in a first cold bath device, and the first cold bath device is connected to a first temperature control device; the pipeline between the first gas storage tank and the methane gas injection pipe is provided with a first gas pressure transmitter;
   the carbon dioxide gas supply device comprises a carbon dioxide gas cylinder; a pipeline, connected to the carbon dioxide gas injection pipe, of the carbon dioxide gas cylinder is provided with a second gas booster pump, a second constant-pressure or constant-rate gas pump and a second gas storage tank in sequence, and the second gas booster pump is close to the carbon dioxide gas cylinder; the second gas storage tank is placed in a second cold bath device, the second cold bath device is connected to a second temperature control device, and the pipeline between the second gas storage tank and the carbon dioxide injection pipe is provided with a second gas pressure transmitter;

the output article collection and measurement device comprises a pressure control valve, preset pressurizing equipment, and an output article collection and measurement assembly; the product discharge hole is connected to the pressure control valve via a pipeline, the pressure control valve is connected to the output article collection and measurement assembly via a pipeline, the output article collection and measurement assembly is configured for collecting and measuring the output article, and the pressure control valve is also connected to the preset pressurizing equipment via a pressure switch; and the temperature and pressure sensor, the axial pressure loading device, the confining pressure loading device, the axial pressure transmitter, the confining pressure transmitter, the first constant-pressure or constant-rate gas pump, the second constant-pressure or constant-rate gas pump, the first temperature control device, the second temperature control device, the first gas pressure transmitter, the second gas pressure transmitter and the output article collection and measurement assembly are electrically connected to the data acquisition control device.

2. The test system for replacing natural gas hydrate with carbon dioxide according to claim 1, wherein a sliding rod is connected to a top end of the axial pressure loading plate, the sliding rod penetrates through the upper cover plate to extend outwards, a through hole penetrating through the sliding rod and the axial pressure loading plate is provided in the sliding rod, the methane gas injection pipe is installed in the through hole, and a lower end of the methane gas injection pipe penetrates through the upper sample-sealing plate to extend to a bottom of the sample-sealing space; a portion, extending into the sample-sealing space, of the methane gas injection pipe is provided with a plurality of gas holes in a height direction of the sample-sealing space, a pipeline holder is installed at a top end of the upper cover plate, and an upper end of the methane gas injection pipe is held and fixed to the pipeline holder.

3. A test method for replacing natural gas hydrate with carbon dioxide based on the test system for replacing natural gas hydrate with carbon dioxide according to claim 2, comprising the following steps:

S1: filling the sample-sealing rubber sleeve with sandy soil sample mixed with deionized water, and installing the sample reaction vessel;

S2: activating the axial pressure loading device and the confining pressure loading device to apply axial pressure and confining pressure on the sandy soil sample simultaneously, making the axial pressure and confining pressure to reach set target pressure values; activating liquid circulation in the liquid cooling jacket to make the temperature in the sample-sealing space to meet a test temperature environment requirement;

S3: vacuumizing the methane gas inlet pipeline, opening the methane gas cylinder, and activating the first gas booster pump, the first constant-pressure or constant-rate gas pump and the first temperature control device, making the methane gas entering the first gas storage tank to reach a set target pressure value and a set target temperature value; injecting the methane gas from the first gas storage tank into the sandy soil sample via the methane gas injection pipe, enabling a reaction to generate a methane hydrate sample, and stopping injecting the methane gas after the reaction is finished; and S4: completely removing air in the carbon dioxide gas inlet pipeline, opening the carbon dioxide gas cylinder, activating the second gas booster pump, the second constant-pressure or constant-rate gas pump and the second temperature control device, making the carbon dioxide gas entering the second gas storage tank to reach a set target pressure value and a set target temperature value; adjusting the preset pressurizing equipment to a pressure value for the carbon dioxide replacement reaction and turning on the pressure switch, injecting the carbon dioxide gas from the second gas storage tank into the methane hydrate sample via the carbon dioxide injection pipe for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device via the product discharge hole, and the output article is collected and measured by the output article collection and measurement assembly.

4. The test system for replacing natural gas hydrate with carbon dioxide according to claim 1, wherein a top end, extending into the sample-sealing space, of the carbon dioxide injection pipe is provided with a plurality of gas holes; the carbon dioxide injection pipe comprises a carbon dioxide injection pipe for an upper portion of sample, a carbon dioxide injection pipe for a middle portion of sample and a carbon dioxide injection pipe for a lower portion of sample, top ends of which extend to an upper portion, a middle portion and a lower portion of the sample-sealing space respectively; a gas outlet pipeline of the second gas storage tank is divided into three branches which are respectively connected to the carbon dioxide injection pipe for an upper portion of sample, the carbon dioxide injection pipe for a middle portion of sample and the carbon dioxide injection pipe for a lower portion of sample, and each branch is provided with a gas injection control valve.

5. The test system for replacing natural gas hydrate with carbon dioxide according to claim 4, wherein the temperature and pressure sensor comprises a temperature and pressure sensor for an upper portion of sample, a temperature and pressure sensor for a middle portion of sample and a temperature and pressure sensor for a lower portion of sample, and measuring probes of the temperature and pressure sensor for an upper portion of sample, the temperature and pressure sensor for a middle portion of sample and the temperature and pressure sensor for a lower portion of sample are respectively located at the upper portion, the middle portion and the lower portion of the sample-sealing space.

6. A test method for replacing natural gas hydrate with carbon dioxide based on the test system for replacing natural gas hydrate with carbon dioxide according to claim 5, comprising the following steps:

S1: filling the sample-sealing rubber sleeve with sandy soil sample mixed with deionized water, and installing the sample reaction vessel;

S2: activating the axial pressure loading device and the confining pressure loading device to apply axial pressure and confining pressure on the sandy soil sample simultaneously, making the axial pressure and confining pressure to reach set target pressure values; activating liquid circulation in the liquid cooling jacket to make the temperature in the sample-sealing space to meet a test temperature environment requirement;

S3: vacuumizing the methane gas inlet pipeline, opening the methane gas cylinder, and activating the first gas booster pump, the first constant-pressure or constant-rate gas pump and the first temperature control device, making the methane gas entering the first gas storage tank to reach a set target pressure value and a set target temperature value; injecting the methane gas from the first gas storage tank into the sandy soil sample via the methane gas injection pipe, enabling a reaction to generate a methane hydrate sample, and stopping injecting the methane gas after the reaction is finished; and S4: completely removing air in the carbon dioxide gas inlet pipeline, opening the carbon dioxide gas cylinder, activating the second gas booster pump, the second constant-pressure or constant-rate gas pump and the second temperature control device, making the carbon dioxide gas entering the second gas storage tank to reach a set target pressure value and a set target temperature value; adjusting the preset pressurizing equipment to a pressure value for the carbon dioxide replacement reaction and turning on the pressure switch, injecting the carbon dioxide gas from the second gas storage tank into the methane hydrate sample via the carbon dioxide injection pipe for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device via the product discharge hole, and the output article is collected and measured by the output article collection and measurement assembly.

7. A test method for replacing natural gas hydrate with carbon dioxide based on the test system for replacing natural gas hydrate with carbon dioxide according to claim 4, comprising the following steps:

S1: filling the sample-sealing rubber sleeve with sandy soil sample mixed with deionized water, and installing the sample reaction vessel;

S2: activating the axial pressure loading device and the confining pressure loading device to apply axial pressure and confining pressure on the sandy soil sample simultaneously, making the axial pressure and confining pressure to reach set target pressure values; activating liquid circulation in the liquid cooling jacket to make the temperature in the sample-sealing space to meet a test temperature environment requirement;

S3: vacuumizing the methane gas inlet pipeline, opening the methane gas cylinder, and activating the first gas booster pump, the first constant-pressure or constant-rate gas pump and the first temperature control device, making the methane gas entering the first gas storage tank to reach a set target pressure value and a set target temperature value; injecting the methane gas from the first gas storage tank into the sandy soil sample via the methane gas injection pipe, enabling a reaction to generate a methane hydrate sample, and stopping injecting the methane gas after the reaction is finished; and S4: completely removing air in the carbon dioxide gas inlet pipeline, opening the carbon dioxide gas cylinder, activating the second gas booster pump, the second constant-pressure or constant-rate gas pump and the second temperature control device, making the carbon dioxide gas entering the second gas storage tank to reach a set target pressure value and a set target temperature value; adjusting the preset pressurizing equipment to a pressure value for the carbon dioxide replacement reaction and turning on the pressure switch, injecting the carbon dioxide gas from the second gas storage tank into the methane hydrate sample via the carbon dioxide injection pipe for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device via the product discharge hole, and the output article is collected and measured by the output article collection and measurement assembly.

8. The test system for replacing natural gas hydrate with carbon dioxide according to claim 1, wherein the output article collection and measurement device further comprises a desander, the desander is arranged on a pipeline between the product discharge hole and the pressure control valve, and a pipeline between the desander and the product discharge hole is provided with an output gas switch valve; the output article collection and measurement assembly comprises a water-gas separator, a gas chromatograph, a gas collection valve, a cold trap treatment device, a gas-liquid separation valve, and a gas collection pump; an inlet of the water-gas separator is connected to an outlet of the pressure control valve, an electronic balance is arranged at a bottom of a water outlet of the water-gas separator, a gas outlet of the water-gas separator is divided into two paths, one path is connected to an inlet of the gas chromatograph via an automatic control valve, and the other path is connected to an inlet of the gas collection valve; an outlet of the gas chromatograph is connected to the inlet of the gas collection valve;

and the gas chromatograph, the cold trap treatment device and the gas collection pump are all electrically connected to the data acquisition control device.

9. The test system for replacing natural gas hydrate with carbon dioxide according to claim 8, wherein the pipeline between the first gas storage tank and the methane gas injection pipe is further provided with a first automatic pressure and gas volume sensor and a methane gas switch valve, and a vacuum pump is further connected to the pipeline between the first gas storage tank and the methane gas injection pipe via a vacuumizing switch valve; the pipeline between the second gas storage tank and the carbon dioxide injection pipe is further provided with a second automatic pressure and gas volume sensor and a carbon dioxide switch valve; a pipeline between the outlet of the gas chromatograph and the inlet of the gas collection valve is further provided with a third automatic pressure and gas volume sensor, and a fourth automatic pressure and gas volume sensor is connected to the tail end of the gas collection pump; and the first automatic pressure and gas volume sensor, the second automatic pressure and gas volume sensor, the third automatic pressure and gas volume sensor and the fourth automatic pressure and gas volume sensor are all electrically connected to the data acquisition control device.

10. The test system for replacing natural gas hydrate with carbon dioxide according to claim 9, wherein the data acquisition control device comprises a multi-path data receiver, a digital closed-loop servo controller and a computer control terminal; the multi-path data receiver and the digital closed-loop servo controller are both electrically connected to the computer control terminal; the first automatic pressure and gas volume sensor, the second automatic pressure and gas volume sensor, the third automatic pressure and gas volume sensor, the fourth automatic pressure and gas volume sensor, the cold trap processing device and the gas collection pump are all electrically connected to the multi-path data receiver; the gas chromatograph is electrically connected to the computer control terminal; the temperature and pressure sensor, the axial pressure loading device, the confining pressure loading device, the axial pressure transmitter, the confining pressure transmitter, the first constant-pressure or constant-rate air pump, the second constant-pressure or constant-rate air pump, the first temperature control device, the second temperature control device, the first air pressure transmitter, and the second gas pressure transmitter are all electrically connected to the digital closed-loop servo controller.

11. A test method for replacing natural gas hydrate with carbon dioxide based on the test system for replacing natural gas hydrate with carbon dioxide according to claim 10, comprising the following steps:
   S1: filling the sample-sealing rubber sleeve with sandy soil sample mixed with deionized water, and installing the sample reaction vessel;
   S2: activating the axial pressure loading device and the confining pressure loading device to apply axial pressure and confining pressure on the sandy soil sample simultaneously, making the axial pressure and confining pressure to reach set target pressure values; activating liquid circulation in the liquid cooling jacket to make the temperature in the sample-sealing space to meet a test temperature environment requirement;
   S3: vacuumizing the methane gas inlet pipeline, opening the methane gas cylinder, and activating the first gas booster pump, the first constant-pressure or constant-rate gas pump and the first temperature control device, making the methane gas entering the first gas storage tank to reach a set target pressure value and a set target temperature value; injecting the methane gas from the first gas storage tank into the sandy soil sample via the methane gas injection pipe, enabling a reaction to generate a methane hydrate sample, and stopping injecting the methane gas after the reaction is finished; and
   S4: completely removing air in the carbon dioxide gas inlet pipeline, opening the carbon dioxide gas cylinder, activating the second gas booster pump, the second constant-pressure or constant-rate gas pump and the second temperature control device, making the carbon dioxide gas entering the second gas storage tank to reach a set target pressure value and a set target temperature value; adjusting the preset pressurizing equipment to a pressure value for the carbon dioxide replacement reaction and turning on the pressure switch, injecting the carbon dioxide gas from the second gas storage tank into the methane hydrate sample via the carbon dioxide injection pipe for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device via the product discharge hole, and the output article is collected and measured by the output article collection and measurement assembly.

12. A test method for replacing natural gas hydrate with carbon dioxide based on the test system for replacing natural gas hydrate with carbon dioxide according to claim 9, comprising the following steps:
   S1: filling the sample-sealing rubber sleeve with sandy soil sample mixed with deionized water, and installing the sample reaction vessel;
   S2: activating the axial pressure loading device and the confining pressure loading device to apply axial pressure and confining pressure on the sandy soil sample simultaneously, making the axial pressure and confining pressure to reach set target pressure values; activating liquid circulation in the liquid cooling jacket to make the temperature in the sample-sealing space to meet a test temperature environment requirement;
   S3: vacuumizing the methane gas inlet pipeline, opening the methane gas cylinder, and activating the first gas booster pump, the first constant-pressure or constant-rate gas pump and the first temperature control device, making the methane gas entering the first gas storage tank to reach a set target pressure value and a set target temperature value; injecting the methane gas from the first gas storage tank into the sandy soil sample via the methane gas injection pipe, enabling a reaction to generate a methane hydrate sample, and stopping injecting the methane gas after the reaction is finished; and
   S4: completely removing air in the carbon dioxide gas inlet pipeline, opening the carbon dioxide gas cylinder, activating the second gas booster pump, the second constant-pressure or constant-rate gas pump and the second temperature control device, making the carbon dioxide gas entering the second gas storage tank to reach a set target pressure value and a set target temperature value; adjusting the preset pressurizing equipment to a pressure value for the carbon dioxide replacement reaction and turning on the pressure switch, injecting the carbon dioxide gas from the second gas storage tank into the methane hydrate sample via the carbon dioxide injection pipe for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device via the product discharge hole, and the output article is collected and measured by the output article collection and measurement assembly.

13. A test method for replacing natural gas hydrate with carbon dioxide based on the test system for replacing natural gas hydrate with carbon dioxide according to claim 8, comprising the following steps:
   S1: filling the sample-sealing rubber sleeve with sandy soil sample mixed with deionized water, and installing the sample reaction vessel;
   S2: activating the axial pressure loading device and the confining pressure loading device to apply axial pressure and confining pressure on the sandy soil sample simultaneously, making the axial pressure and confining pressure to reach set target pressure values; activating liquid circulation in the liquid cooling jacket to make the temperature in the sample-sealing space to meet a test temperature environment requirement;

S3: vacuumizing the methane gas inlet pipeline, opening the methane gas cylinder, and activating the first gas booster pump, the first constant-pressure or constant-rate gas pump and the first temperature control device, making the methane gas entering the first gas storage tank to reach a set target pressure value and a set target temperature value; injecting the methane gas from the first gas storage tank into the sandy soil sample via the methane gas injection pipe, enabling a reaction to generate a methane hydrate sample, and stopping injecting the methane gas after the reaction is finished; and S4: completely removing air in the carbon dioxide gas inlet pipeline, opening the carbon dioxide gas cylinder, activating the second gas booster pump, the second constant-pressure or constant-rate gas pump and the second temperature control device, making the carbon dioxide gas entering the second gas storage tank to reach a set target pressure value and a set target temperature value; adjusting the preset pressurizing equipment to a pressure value for the carbon dioxide replacement reaction and turning on the pressure switch, injecting the carbon dioxide gas from the second gas storage tank into the methane hydrate sample via the carbon dioxide injection pipe for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device via the product discharge hole, and the output article is collected and measured by the output article collection and measurement assembly.

14. The test system for replacing natural gas hydrate with carbon dioxide according to claim 1, wherein the axial pressure loading device comprises a first large-displacement continuous liquid supply plunger pump set and a first pressure servo continuous liquid supply plunger pump set, inlets of the first large-displacement continuous liquid supply plunger pump set and the first pressure servo continuous liquid supply plunger pump set are connected to an oil source, and outlets of the first large-displacement continuous liquid supply plunger pump set and the first pressure servo continuous liquid supply plunger pump set are divided into two paths comprising an axial pressure loading pipeline and an axial pressure unloading pipeline; the axial pressure loading pipeline is connected to the axial pressure loading injection hole and is provided with an axial pressure loading control valve, and the axial pressure unloading pipeline is connected to the oil source and is provided with an axial pressure unloading control valve; the confining pressure loading device comprises a second large-displacement continuous liquid supply plunger pump set and a second pressure servo continuous liquid supply plunger pump set, inlets of the second large-displacement continuous liquid supply plunger pump set and the second pressure servo continuous liquid supply plunger pump set are connected to the oil source, and outlets of the second large-displacement continuous liquid supply plunger pump set and the second pressure servo continuous liquid supply plunger pump set are divided into two paths comprising a confining pressure loading pipeline and a confining pressure unloading pipeline;

the confining pressure loading pipeline is connected to the confining pressure loading injection hole and is provided with a confining pressure loading control valve, and the confining pressure unloading pipeline is connected to the oil source and is provided with a confining pressure unloading control valve.

15. A test method for replacing natural gas hydrate with carbon dioxide based on the test system for replacing natural gas hydrate with carbon dioxide according to claim 14, comprising the following steps:

S1: filling the sample-sealing rubber sleeve with sandy soil sample mixed with deionized water, and installing the sample reaction vessel;

S2: activating the axial pressure loading device and the confining pressure loading device to apply axial pressure and confining pressure on the sandy soil sample simultaneously, making the axial pressure and confining pressure to reach set target pressure values; activating liquid circulation in the liquid cooling jacket to make the temperature in the sample-sealing space to meet a test temperature environment requirement;

S3: vacuumizing the methane gas inlet pipeline, opening the methane gas cylinder, and activating the first gas booster pump, the first constant-pressure or constant-rate gas pump and the first temperature control device, making the methane gas entering the first gas storage tank to reach a set target pressure value and a set target temperature value; injecting the methane gas from the first gas storage tank into the sandy soil sample via the methane gas injection pipe, enabling a reaction to generate a methane hydrate sample, and stopping injecting the methane gas after the reaction is finished; and S4: completely removing air in the carbon dioxide gas inlet pipeline, opening the carbon dioxide gas cylinder, activating the second gas booster pump, the second constant-pressure or constant-rate gas pump and the second temperature control device, making the carbon dioxide gas entering the second gas storage tank to reach a set target pressure value and a set target temperature value; adjusting the preset pressurizing equipment to a pressure value for the carbon dioxide replacement reaction and turning on the pressure switch, injecting the carbon dioxide gas from the second gas storage tank into the methane hydrate sample via the carbon dioxide injection pipe for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device via the product discharge hole, and the output article is collected and measured by the output article collection and measurement assembly.

16. The test system for replacing natural gas hydrate with carbon dioxide according to claim 1, wherein an outlet pipeline of the methane gas cylinder is provided with a first pressure regulating valve, an inlet pipeline and an outlet pipeline of the first gas booster pump are respectively provided with a first gas switch valve and a second gas switch valve; an outlet pipeline of the carbon dioxide gas cylinder is provided with a second pressure regulating valve, and an inlet pipeline and an outlet pipeline of the second gas booster pump are respectively provided with a third gas switch valve and a fourth gas switch valve.

17. A test method for replacing natural gas hydrate with carbon dioxide based on the test system for replacing natural gas hydrate with carbon dioxide according to claim 16, comprising the following steps:

S1: filling the sample-sealing rubber sleeve with sandy soil sample mixed with deionized water, and installing the sample reaction vessel;

S2: activating the axial pressure loading device and the confining pressure loading device to apply axial pressure and confining pressure on the sandy soil sample simultaneously, making the axial pressure and confining pressure to reach set target pressure values; activating liquid circulation in the liquid cooling jacket to make the temperature in the sample-sealing space to meet a test temperature environment requirement;

S3: vacuumizing the methane gas inlet pipeline, opening the methane gas cylinder, and activating the first gas booster pump, the first constant-pressure or constant-rate gas pump and the first temperature control device, making the methane gas entering the first gas storage tank to reach a set target pressure value and a set target temperature value; injecting the methane gas from the first gas storage tank into the sandy soil sample via the methane gas injection pipe, enabling a reaction to generate a methane hydrate sample, and stopping injecting the methane gas after the reaction is finished; and S4: completely removing air in the carbon dioxide gas inlet pipeline, opening the carbon dioxide gas cylinder, activating the second gas booster pump, the second constant-pressure or constant-rate gas pump and the second temperature control device, making the carbon dioxide gas entering the second gas storage tank to reach a set target pressure value and a set target temperature value; adjusting the preset pressurizing equipment to a pressure value for the carbon dioxide replacement reaction and turning on the pressure switch, injecting the carbon dioxide gas from the second gas storage tank into the methane hydrate sample via the carbon dioxide injection pipe for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device via the product discharge hole, and the output article is collected and measured by the output article collection and measurement assembly.

18. A test method for replacing natural gas hydrate with carbon dioxide based on the test system for replacing natural gas hydrate with carbon dioxide according to claim 1, comprising the following steps:

S1: filling the sample-sealing rubber sleeve with sandy soil sample mixed with deionized water, and installing the sample reaction vessel;

S2: activating the axial pressure loading device and the confining pressure loading device to apply axial pressure and confining pressure on the sandy soil sample simultaneously, making the axial pressure and confining pressure to reach set target pressure values; activating liquid circulation in the liquid cooling jacket to make the temperature in the sample-sealing space to meet a test temperature environment requirement;

S3: vacuumizing the methane gas inlet pipeline, opening the methane gas cylinder, and activating the first gas booster pump, the first constant-pressure or constant-rate gas pump and the first temperature control device, making the methane gas entering the first gas storage tank to reach a set target pressure value and a set target temperature value; injecting the methane gas from the first gas storage tank into the sandy soil sample via the methane gas injection pipe, enabling a reaction to generate a methane hydrate sample, and stopping injecting the methane gas after the reaction is finished; and S4: completely removing air in the carbon dioxide gas inlet pipeline, opening the carbon dioxide gas cylinder, activating the second gas booster pump, the second constant-pressure or constant-rate gas pump and the second temperature control device, making the carbon dioxide gas entering the second gas storage tank to reach a set target pressure value and a set target temperature value; adjusting the preset pressurizing equipment to a pressure value for the carbon dioxide replacement reaction and turning on the pressure switch, injecting the carbon dioxide gas from the second gas storage tank into the methane hydrate sample via the carbon dioxide injection pipe for enabling the carbon dioxide replacement reaction, and stopping injecting the carbon dioxide gas after the replacement reaction is finished, wherein the gas mixture of methane and carbon dioxide generated by the replacement reaction enters the output article collection and measurement device via the product discharge hole, and the output article is collected and measured by the output article collection and measurement assembly.

\* \* \* \* \*